United States Patent
Whalen et al.

(10) Patent No.: US 8,016,742 B2
(45) Date of Patent: *Sep. 13, 2011

(54) ENDOURETHRAL DEVICE AND METHOD

(75) Inventors: Mark J. Whalen, Alexandria, MN (US);
Lloyd K. Willard, Miltona, MN (US);
John M. Reid, Garfield, MN (US)

(73) Assignee: AbbeyMoor Medical, Inc., Parkers Prairie, MN (US)

( * ) Notice: Subject to any disclaimer, the term of this patent is extended or adjusted under 35 U.S.C. 154(b) by 1523 days.

This patent is subject to a terminal disclaimer.

(21) Appl. No.: 11/413,540

(22) Filed: Apr. 28, 2006

(65) Prior Publication Data

US 2006/0195008 A1   Aug. 31, 2006

Related U.S. Application Data

(63) Continuation of application No. 10/059,100, filed on Jan. 23, 2002, now Pat. No. 7,108,655.

(60) Provisional application No. 60/263,202, filed on Jan. 23, 2001, provisional application No. 60/295,535, filed on Jun. 4, 2001, provisional application No. 60/329,859, filed on Oct. 18, 2001.

(51) Int. Cl.
*A61F 2/02* (2006.01)

(52) U.S. Cl. .......................................... 600/30

(58) Field of Classification Search .............. 600/29–31, 600/433–435, 483–486, 505–507, 560–561, 600/568–591; 128/DIG. 25, 885–886; 604/915, 604/919, 920, 327, 329

See application file for complete search history.

(56) References Cited

U.S. PATENT DOCUMENTS

| | | |
|---|---|---|
| 4,233,983 A | 11/1980 | Rocco |
| 4,932,938 A | 6/1990 | Goldberg et al. |
| 4,973,301 A | 11/1990 | Nissenkorn |
| 5,096,454 A | 3/1992 | Samples |
| 5,234,409 A | 8/1993 | Goldberg et al. |
| 5,269,802 A | 12/1993 | Garber |
| 5,306,241 A | 4/1994 | Samples |
| 5,322,501 A | 6/1994 | Mahmud-Durrani |
| 5,466,222 A | 11/1995 | Ressermann et al. |
| 5,746,720 A | 5/1998 | Stouder, Jr. |
| RE35,849 E | 7/1998 | Soehendra |
| 5,785,641 A | 7/1998 | Davis |
| 5,795,288 A | 8/1998 | Cohen et al. |
| 5,846,259 A | 12/1998 | Berthiaume |
| 6,179,827 B1 | 1/2001 | Davis et al. |
| 6,494,879 B2 | 12/2002 | Lennox et al. |

(Continued)

FOREIGN PATENT DOCUMENTS

EP    0 266 091 A2    5/1988

(Continued)

*Primary Examiner* — John Lacyk
(74) *Attorney, Agent, or Firm* — Nawrocki, Rooney & Sivertson, P.A.

(57) ABSTRACT

An endourethral device is provided having an elongate member having proximal and distal segments, the elongate member positionable within a lower urinary tract so as to at least partially traverses a prostatic urethra. A proximal anchor, adapted to abuttingly engage portions of a bladder neck so as to at least proximally anchor the device, is supported at least indirectly by the proximal segment of said elongate member. The proximal anchor includes bladder engaging elements radially extending from the proximal segment of said elongate member, urine being freely dischargable about at least the proximal segment so as to substantially bathe the bladder neck therewith.

31 Claims, 6 Drawing Sheets

U.S. PATENT DOCUMENTS

| | | |
|---|---|---|
| 6,866,682 B1 | 3/2005 | An et al. |
| 6,991,596 B2 * | 1/2006 | Whalen et al. .................. 600/30 |
| 7,131,996 B2 | 11/2006 | Wasserman et al. |
| 7,141,038 B2 * | 11/2006 | Whalen et al. ............. 604/99.01 |
| 7,320,710 B2 | 1/2008 | Rioux et al. |
| 7,442,721 B2 * | 10/2008 | Cheng et al. ................ 514/772.4 |

FOREIGN PATENT DOCUMENTS

| | | |
|---|---|---|
| EP | 1 062 920 A1 | 12/2000 |
| JP | 02-107274 | 4/1990 |
| JP | 2523436 | 10/1996 |
| JP | 11-512635 | 11/1999 |
| JP | 2001-502560 | 2/2001 |
| JP | 2001-104325 | 4/2001 |
| WO | WO-9712562 A1 | 4/1997 |
| WO | WO 98/00192 A1 | 1/1998 |
| WO | WO-9800192 A1 | 1/1998 |
| WO | WO 98/05268 A1 | 2/1998 |
| WO | WO-9805268 A1 | 2/1998 |
| WO | WO 98/37834 A1 | 9/1998 |
| WO | WO 99/08741 A1 | 2/1999 |
| WO | WO-0056246 A1 | 9/2000 |

* cited by examiner

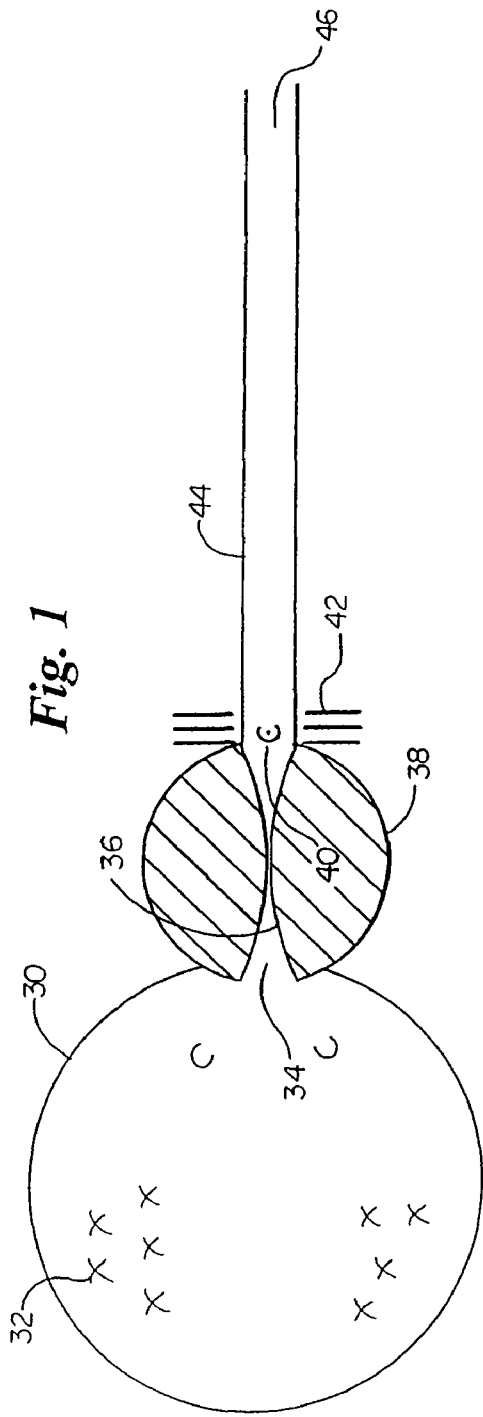
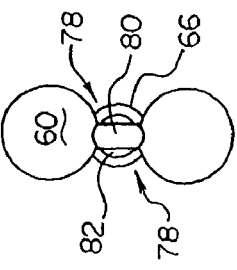
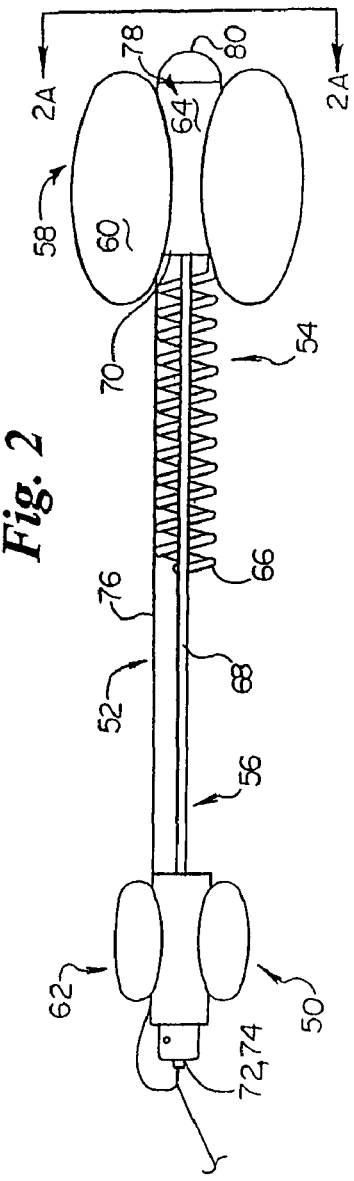
Fig. 1
Fig. 2
Fig. 2A

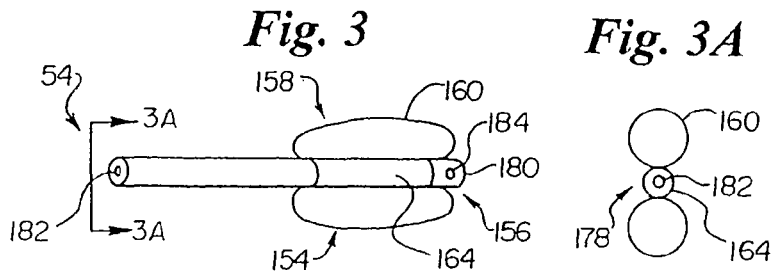
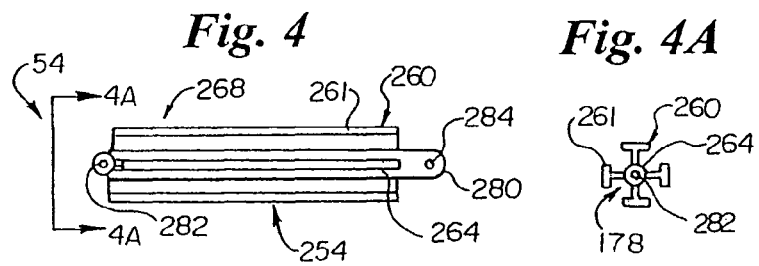
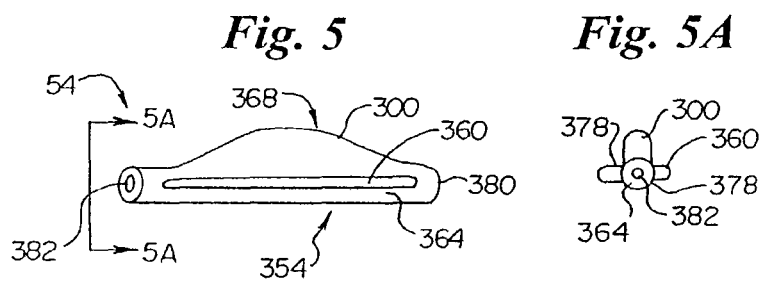
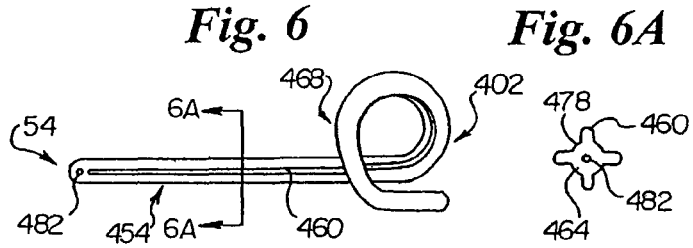
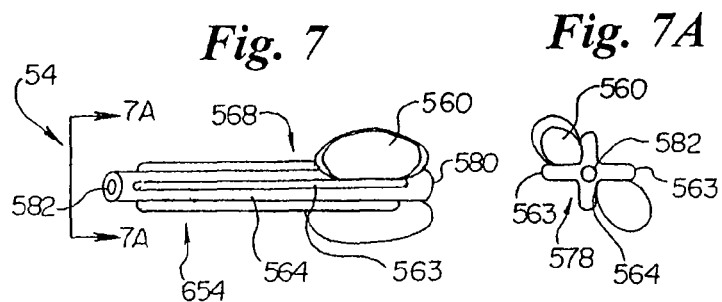

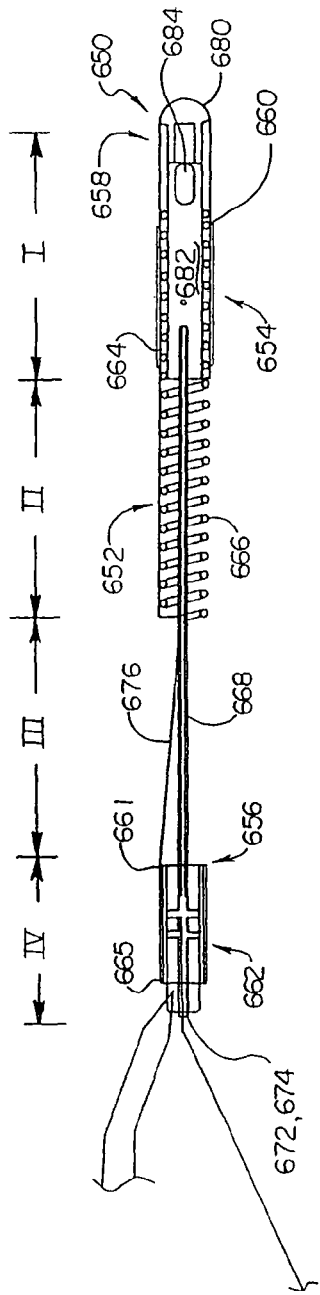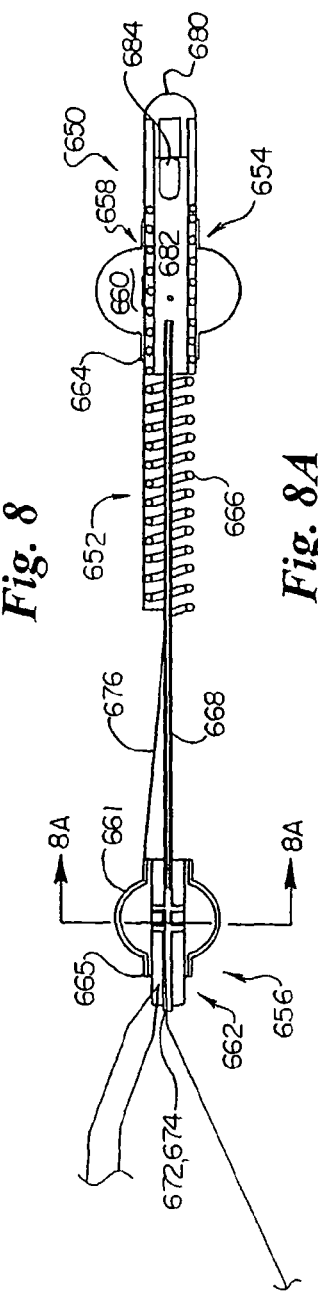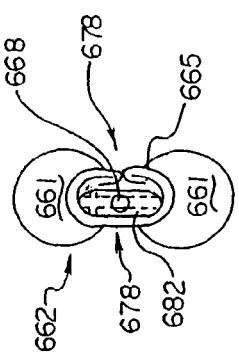

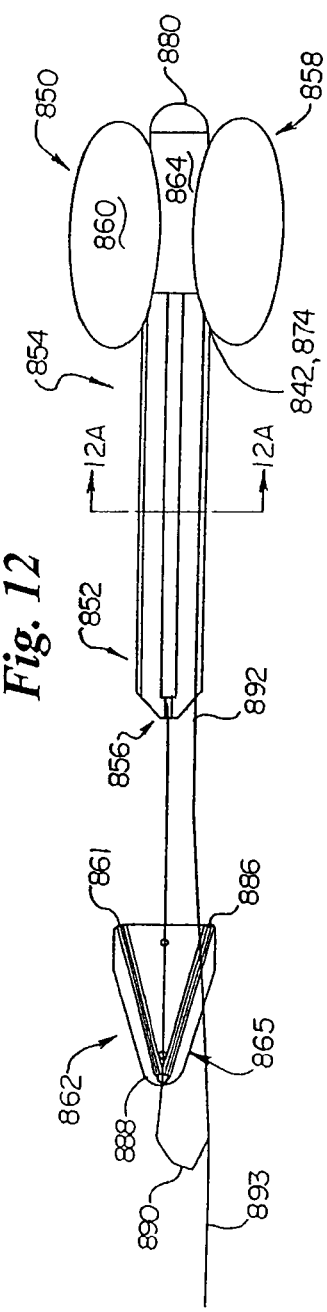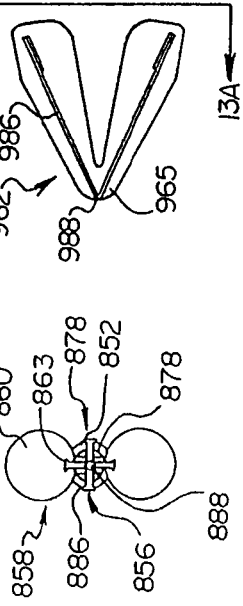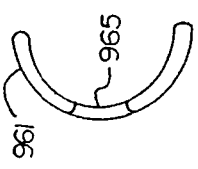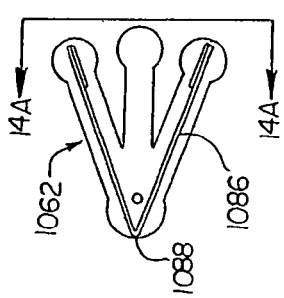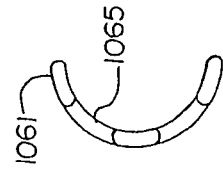

ENDOURETHRAL DEVICE AND METHOD

This is a continuing application filed under 37 CFR §1.53 (b) of a regular application Ser. No. 10/059,100, filed Jan. 23, 2002 now U.S. Pat. No. 7,108,655 under 35 U.S.C. §111(a) claiming priority under 35 U.S.C. §119(e)(1), of provisional application Ser. No. 60/263,202, having a filing date of Jan. 23, 2001; provisional application Ser. No. 60/295,535, having a filing date of Jun. 4, 2001; and, provisional application Ser. No. 60/329,859, having a filing date of Oct. 18, 2001, all of which were filed pursuant to 35 U.S.C. §111(b).

TECHNICAL FIELD

The present invention generally relates to medical devices, more particularly to endourethral devices, and still more particularly to endourethral devices having anchor structures which permit the discharge of urine therethrough and/or there around.

BACKGROUND OF THE INVENTION

Urinary problems can have serious consequences, particularly when the problem is one of retention, incomplete emptying, or dysuria. Urine flow problems include urine retention, incontinence, and difficult urination. Retention can result from any of a number of causes, including without limitation, spinal cord injury, typhoid, peritonitis, prostatic enlargement, urethral stricture, urethritis, cystitis, bladder tumors, or urethral calculus. Patients suffering from these and other conditions often require some interventional means to periodically drain or augment drainage of the bladder. Failure to do so can result in damage of the epithelium and detrusor muscles associated with the bladder, and an increased potential for bacterial invasion which is commonly thought to contribute to urinary tract infection potentially leading to life-threatening kidney failure.

Beyond notions of intervention, in roads are presently being made in the area of office and office/home based monitoring of patients for purpose of diagnosing the contribution of the prostatic urethra to the outflow urodynamics. Differential diagnosis is understood by accepting that there are three primary anatomical organs which interact to contribute to the function of urination. First the bladder, second the urethra, and third the sphincter(s). The prostatic gland surrounds the urethra in the very short segment between the bladder, at its outlet, and the external sphincter. When the patient experiences symptoms of bother which may be made manifest in several independent or co-existing difficulties during urination, treatment is often sought.

For example, bothersome symptoms might include: (i) incomplete emptying, (i.e., the patient is only able to urinate small volumes, e.g. <100 milliliters (ml), or has an elevated volume of urine left in the bladder following urination, e.g. >100 ml. per attempt); (ii) frequent urges to urinate (i.e., experiencing a frequent feeling of needing to urinate by an individual); (iii) intermittency (e.g. a patient's flow stops and starts often during urination); (iv) has a very weak and inconsistent urine flow stream; (v) stress incontinence (e.g. leaking during lifting or straining as a result of excessive urine in the bladder or weakened sphincters. With the exception of stress incontinence, each of these may contribute to nocturia (i.e., poor sleep due to the repeated need to urinate during the night), yet a further symptom.

Up to two million office visits annually in the United States are attributed to patients being bothered by some form of lower urinary tract symptoms (LUTS). As previously noted, there are two primary organs, and the prostate, involved with the event of urination. The symptoms are virtually always suspected to be caused by the intrusion of an enlarged prostate gland upon the urethra, however, symptoms are often caused by irregularities in bladder function, or sphincter deficiencies. For this reason, bladder outlet obstructions (BOO) is a major subgroup of LUTS. In men between the ages of 55 and 75 years, it is estimated that between 50 and 75% have some degree of bladder outlet obstruction, however, it may not be responsible for their symptoms.

Bladder outlet obstructions are primarily caused by the enlargement of the prostate gland (e.g., benign prostate hyperplasia (BHP)) which results in radial compression of the urethra surrounded thereby (i.e., the prostatic urethra), thus obstructing (i.e., constricting) urine flow, resulting in incomplete emptying of the bladder (i.e., there being what is clinically referred to as a "post void residual" (PVR) remaining in the bladder). Heretofore, males presenting with LUTS have few diagnostic options prior to either long term pharmacological, or invasive irreversible medical procedures such as trans urethral resection of the prostate (TURP), or non-surgical procedures such as thermal treatment of the prostate.

It is well known within the urological community that significant numbers of men undergoing treatment for prostate disease have sub-optimal results. According to Bruskewitz, benign prostatic hyperplasia (BPH) can be discussed in terms of prostatic enlargement, outlet obstruction and lower urinary tract symptoms (LUTS). Jepsen J. V. and Bruskewitz R. C., *Comprehensive Patient Evaluation for Benign Prostatic Hyperplasia,* 1998, Urology 51 (A4):13-18. In addition to the usual factors believed to lead to prostate induced LUTS (e.g., enlarged prostate and increased prostate muscle tone) other conditions of the lower urinary tract impact male voiding and need to be considered. Bruskewitz stated that a large part of the symptomotology of BPH might be explained by bladder dysfunction.

Bladder conditions that are prevalent in men with LUTS, either separately or in combination with outlet obstruction, include detrusor instability and detrusor hypocontractility. Kaplan S. A. and, Te A. E., *Uroflowmetry and Urodynamics,* 1995, Urologic Clinics of North America 22 (2):309-320. In a population of 787 men with symptoms of prostatism, Kaplan found that 504 (64%) had demonstrable prostatic urethral obstruction, of which 318 had concomitant detrusor instability. In the group, 181 had detrusor instability as their sole diagnosis. Impaired detrusor contractility was present in 134 (17%) and 49 of these had impaired detrusor contractility as their only diagnosis. Bruskewitz and others have also shown that a significant number of men with LUTS, including those who receive definitive treatment, are unobstructed. Abrams P., *In Support of Pressure Flow Studies for Evaluating Men with Lower Urinary Tract Symptoms,* 1994, Urology 44 (2): 153-55. Patient satisfaction rates after definitive prostate treatment vary from 100% to 75% or less. In some cases the lack of success may be related to unidentified bladder dysfunction. Bruskewitz concluded that bladder dysfunction should receive more attention (in the evaluation and treatment of LUTS) and better measures should be developed to quantify it. Presently, urodynamic methods to assess bladder outlet obstruction generally include uroflow testing, pressure flow testing and general patient history/examination.

Uroflow testing provides information about the combined contribution of the detrusor and urethra to uroflow. The limitation of uroflow testing is that it is not possible to determine with certainty in all cases whether a low flow and a poor voiding pattern are secondary to outlet obstruction, detrusor hypocontractility or a combination thereof. Further, the test can be problematic because it is only a single event that can be influenced by patient factors such as anxiety and performance of the test (i.e. direction of the urine steam into the collecting reservoir). Abrams found that the success rate was only 70% when uroflow was used to select patients for surgery. Abrams P. H., *Prostatism and Prostatectomy: The Value of Flow Rate Measurement in the Preoperative Assessment for Operation.* J. Urol 1977, 177:70-71.

Pressure flow testing can be used to define outlet obstruction and, in addition, provides information about the contractility and performance of the bladder. The pressure flow test, however, is not much more successful in predicting success of treatment, as defined by the patient, than uroflow (75% v 64%). Jepsen J. V. and Bruskewitz R. C., *Comprehensive Patient Evaluation for Benign Prostatic Hyperplasia*, 1998, Urology 51 (A4):13-18. Therefore the urological community as well as the Agency for Healthcare Policy & Research (AHCPR) do not find justification for its routine use.

Finally, the standard work-up of patients with LUTS being evaluated for bladder outlet obstruction generally consists of history and physical examination, including assessment of prostate volume, PSA, uroflow testing, quality of life, and symptom and bother index. Based on the results, treatment decision are made. Using these evaluations underlying problems with bladder function cannot be detected.

In lieu of traditional urodynamic test methodologies such as the use of video urodynamics simultaneously with the holding and release of urine, cystometry, urethral pressure profiling, ultrasonic volume assessments (i.e., PVR), and uroflowmetry, each of which address the filing/emptying conditions (i.e., dynamics) of the bladder, endourethral devices and accompanying methodologies have been developed specifically to ascertain the nature of the BOO. For instance by permitting the structures of the lower urinary tract to physiologically act in a sequential and incremental manner upon portions of a device during a natural micturition event, an observable change in fluid dynamics in furtherance of lower urinary tract symptoms diagnosis may be noted.

Devices have been developed to be positioned in the urethra and/or bladder to correct the problems of urine flow. Problems and disadvantages of heretofore known devices include the deleterious effects (i.e., pitting, depositions, etc.) associated with the urethral environment upon critical device components (e.g., valve actuators, flow conduits, etc.) which at a minimum render such devices less effective, and which at a maximum, cause device component failure or render the device wholly ineffective, which necessitates emergent removal and, as the case may be, urinary tract damage repair. Problems of device leakage, or less than complete emptying of the bladder are also widely known. Furthermore, issues surrounding device deployment and fit, positioning, repositioning, and retention (i.e., sufficient anchoring) have also been well documented.

It is especially critical that the endourethral device be stable with respect to position (i.e., a physiologically properly deployed and stable position), and comfortable to wear, as the urinary tract is sensitive to contact. Inter-urethral stents have been utilized within the male urethra within the prostatic region with many users foregoing such devices for alternate therapies due to feelings of discomfort and/or pain. Many endourethral devices have similarly been evaluated for urinary incontinence for females. Based upon clinical findings, many have been shown to be uncomfortable, thus severely retarding their utility as a therapy. Other devices have migrated into the bladder, or have been expelled under straining conditions.

Furthermore, it is imperative that the device be no more invasive as is necessary. For instance, it is advantageous that the device minimally engage the structures of the lower urinary tract, particularly in accomplishing an anchoring function. For example, it is well known that secretions of the prostatic urethra, including the Cooper's gland, whether during sexual function or otherwise, is clinically beneficial, the secretions are comprised, in part, of antimicrobial agents which assist in the prevention of urinary tract infections. It is further believed that bathing of the bladder neck with urine assists infection prevention. Generally, flow of urine external of an endourethral device permits the free passage of urinary tract fluids from the urethra as urine is released, thereby allowing a more physiologically normal urine discharge. Thus, whether it be a short or long term endourethral device, for interventional, diagnostic or other purpose, stable anchoring in combination with physiologically proper, non-traumatic device deployment and retention is essential.

SUMMARY OF THE INVENTION

An endourethral device is generally provided having an elongate member including proximal and distal segments, the elongate member positionable within a lower urinary tract so as to at least partially traverse a prostatic urethra. A proximal anchor, adapted to abuttingly engage portions of a bladder neck so as to at least proximally anchor the device, is supported at least indirectly by the proximal segment of the elongate member. The proximal anchor includes bladder engaging elements radially extending from a portion of the proximal segment of the elongate member, urine being freely dischargable about at least the proximal segment so as to substantially bathe the bladder neck therewith.

The devices of the several embodiments of the subject invention are especially suited for temporary, short term use as wearable urodynamic devices which allow patient initiated urination in men with lower urinary tract symptoms (LUTS) or symptoms of prostatism so as to support open the prostatic urethra, thereby permitting temporarily relief or modification of symptoms, and discretionary clinician-patient collaborative monitoring and assessment of symptoms for the purpose of evaluating the contribution of the bladder and the bladder outlet to uroflow, urine voiding patterns and symptoms.

Preferably, the device is positioned to traverse the prostatic urethra from the bladder neck to the proximal side of the urinary sphincter, being held in position by a balloon on its proximal end, and a soft silicone anchor on the distal end. Similar to a Foley-type catheter, the 5 cc balloon on the proximal tip is positioned in the bladder neck to provide retention of the endourethral device. The silicone anchor is attached to the distal end of the endourethral device by means of a suture. The length of the suture is such that it traverses the length of the sphincter, positioning the anchor on the distal side of the sphincter to prevent migration inward to the bladder. Once positioned, the endourethral device conducts urine flow across the prostatic urethra during the physiologic functioning of bladder contraction and sphincter relaxation, removing the influence of potential prostatic urethral obstruction on voiding function. By providing a fixed orifice through the desired segment of the prostatic urethra during standard uroflow testing and at home monitoring, the endourethral device permits information acquisition about bladder function not currently obtainable with heretofore known structures and/or methodologies.

Specifically, if obstruction is present, it provides a fixed orifice through the obstructing component to allow relief evaluation of the bladder and sphincter components of voiding separately, while potentially providing relief of the accompanying symptoms. By conducting uroflow testing with and without a endourethral device in place, the urologist can gain information about whether a disturbance of flow rate and the voiding pattern is likely due to an obstructed prostatic urethra or underlying bladder dysfunction. As an example, if decreased flow is solely due to an obstructing prostatic urethra, the flow rate would be expected to increase and the flow pattern to become more normal when voiding is evaluated with a Endourethral device in place. Conversely, if decreased flow is primarily related to dysfunction of the bladder, or a combination of bladder dysfunction and obstruction, the flow rate and pattern would not be expected to normalize with a endourethral device in place.

Currently, the presence of symptoms or the bother to the patient from symptoms is the key deciding factor in the decision for treatment and, as well, symptoms and the bother from symptoms are the key outcomes used to determine success of treatment. If at home monitoring of voiding patterns and urinary symptoms (e.g., voided volumes, frequency, urgency, nocturia, strength of stream) is done with and without an endourethral device inserted, information can be gained about the contribution of the prostatic urethra (obstruction) to those parameters, providing important information not currently available.

As will become apparent, the temporary endourethral devices of the subject invention have a number of potential clinical applications. These include temporary treatment of acute retention patients until flow is reestablished, home and office monitoring of patient uroflow and symptoms, or potentially longer term use for patients who are poor surgical risk, or in waiting for therapy. The endourethral devices of these embodiments functionally provide the necessary attributes to meet each of these clinical applications. Enablement of treating each of the aforementioned clinical needs is in the pioneer stage with no devices currently FDA approved or marketed in the U.S. Of the three listed clinical needs, none is newer, or the clinical implications more promising than the use of the subject invention in all its embodiments and permutations for combined treatment and monitoring for the purpose of providing additional data and information to be used for the purpose of differential diagnosis.

BRIEF DESCRIPTION OF THE DRAWINGS

FIG. 1 schematically depicts the human male urinary bladder and urinary passage;

FIG. 2 illustrates an endourethral device of the subject invention, particularly showing "flow by" proximal and distal anchor systems;

FIG. 2A is a section view of the device of FIG. 2 taken about line 2A-2A, more particularly, a sectional view of the proximal anchor of same;

FIG. 3-7 illustrate alternate configurations for the proximal anchor of the device of the subject invention;

FIGS. 3A-7A are sectional views corresponding to the alternate configurations for the proximal anchors of FIGS. 3-7;

FIG. 8 is a longitudinal cross section of an alternate embodiment of the device of the subject invention, the anchor elements in extension;

FIG. 8A is a section view of the device of FIG. 8 taken about line 8A-8A, more particularly, a sectional view of the distal anchor of same;

FIG. 9 is a view of the device of FIG. 8, the anchor elements in retraction;

FIG. 12 illustrates an alternate embodiment of the endourethral device of the subject invention, particularly illustrating a distal mechanical anchor along with a proximal anchor element in extension, lateral flow permitted;

FIG. 12A is a section view of the device of FIG. 12 taken about line 12A-12A; and, FIGS. 13-20 illustrate alternate configurations for the mechanical distal anchor, accompanying alpha designated figures depicting corresponding sectional views.

DETAILED DESCRIPTION OF THE INVENTION

Figure 10:
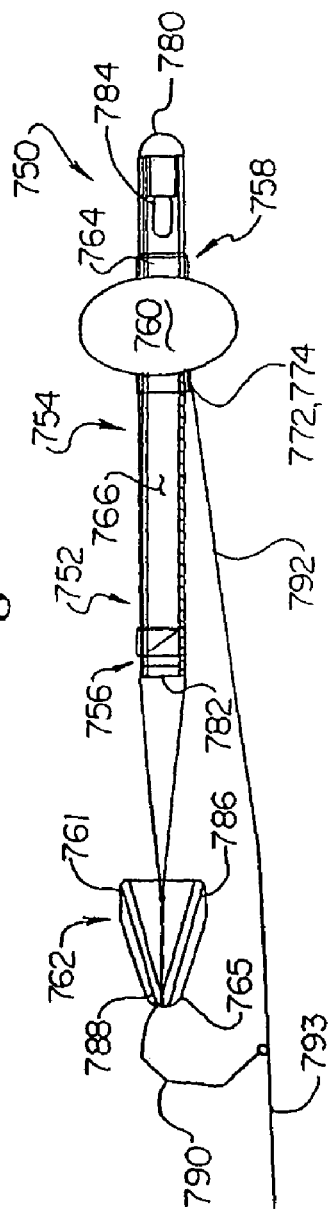
FIG. 10 illustrates an alternate embodiment of the endourethral device of the subject invention, particularly illustrating a distal mechanical anchor, a proximal anchor element in extension.
Figure 11:
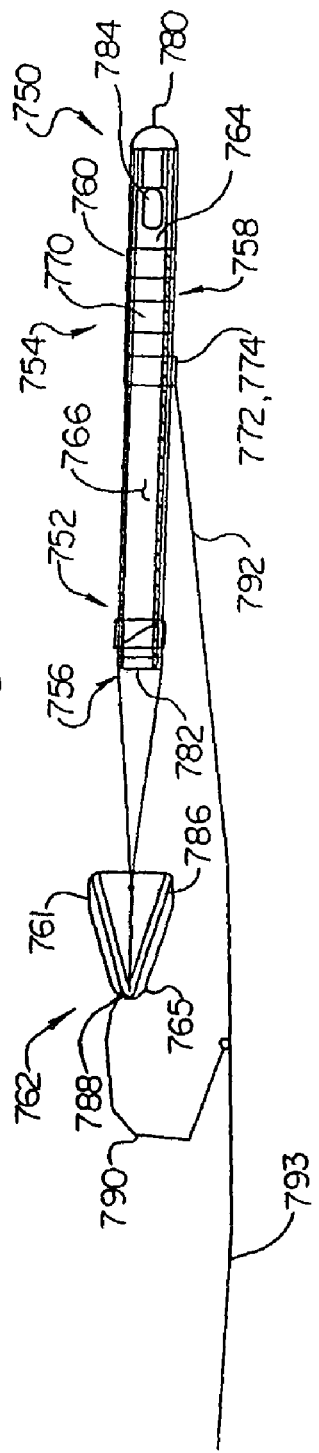
FIG. 11 is a view of the device of FIG. 10, the proximal anchor element in retraction.

A schematic of the human male urinary bladder and urinary passage (i.e., the lower urinary tract) is presented in FIG. 1. The bladder 30 temporarily stores urine 32 and periodically expels it when the bladder neck 34 opens, as the bladder 30 contracts. Urine 32 passes through the prostatic urethra 36, which is completely surrounded by the prostate 38. The distal limit of prostate 38 is marked by a small projection called the verumontanum 40. This is a important landmark because distal thereto, is the external urethral sphincter 42, which relaxes soon after the urination process begins. Beyond this is the urethra 44, affording a free passage of urine 32 external to body, beyond the external urethral meatus 46.

Generally referencing FIG. 2 (see also FIGS. 8, 10 & 12 having reference numerals +600, +700, and +800 respectively for like structures), there is shown an endourethral device 50 which generally comprises an elongate member 52 having proximal 54 and distal 56 segments, the elongate member 52 being positionable within the lower urinary tract so as to at least partially traverse the prostatic urethra. A proximal anchor 58, adapted to preferably abuttingly engage portions of the bladder neck so as to at least proximally anchor the device, is supported at least indirectly by the proximal segment 54 of the elongate member 52. The proximal anchor 58 includes bladder engaging elements 60 radially extending from a portion of the proximal segment 54 of the elongate member 52, urine being freely dischargable about at least the proximal segment 54 so as to substantially bathe the bladder neck therewith. Preferably, but not necessarily, the bladder engaging elements 60 radially extending from a body 64 of the proximal anchor 58 such that urine is freely dischargable about or around an exterior surface of the anchor body 64. A distal anchor 62, adapted to engage portions of the bulbous urethra so as to at least distally anchor the device, is supported by at least a portion of the distal segment 56 of the elongate element 52. The elongate member 52, may alternately be interposed (FIGS. 2 & 8), or at least indirectly extend (FIGS. 10 & 12) between proximal and distal anchor elements or structures, as will be subsequently described.

As may be apparent from the aforementioned description, it is to be understood that the configuration or overall structure of the elongate member is highly variable, being dependent upon the sought after functionality of the endourethral device (i.e., the physiological condition being diagnosed and or treated). In an interventional setting, the elongate member generally provides a degree of support to assure patency of an intact but contracted lumen, see for example co-pending PCT Application No. 01/24817 entitled ENDOURETHRAL DEVICE & METHOD, incorporated herein by reference. Alternately, in a diagnostic setting for instance, the elongate member may comprise a selectively radial responsive segment for engagement with a portion of the urethra, namely the prostatic urethra. The radial responsive segment or diaphragm possesses a dual functionality, namely selective inward and outward radial responsiveness, in furtherance of qualitatively and/or quantitatively assessing fluid pressure and/or fluid flow through portions of the lower urinary tract, and memorializing the nature of the urethral structures (i.e., the architecture of the prostatic urethra and the relationship between the structures thereof) as by obtaining a casting, respectively, see for example, co-pending U.S. patent application Ser. No. 09/943,975 entitled DIAGNOSTIC URETHRAL ASSEMBLY & METHOD, incorporated herein by reference.

Referring now to FIGS. 2 & 2A, the endourethral device (i.e., stent) shown includes a distal anchor 62 adapted to engage portions of the bulbous urethra, and a proximal anchor 58 adapted to abuttingly engage the bladder neck, the anchors being linked by a support element or structure 52. As aforementioned, form fits function relative to the elongate member or central segment of the endourethral device, in this instance a support element which includes a structurally supportive body 66 which is preferably coil wound of 0.012 inch round stainless steel which has been silicone encapsulated. A fluid conduit 68, to facilitate expansion of the reversibly expansive bladder engaging elements 60, distally extends along a longitudinal device axis from a filling manifold 70 to distal anchor 62. Emptying of the fluid system is accomplished by removing a plug 72 from a drain port 74 integral to at least the distal segment 56 of the elongate member 52, consistent with the methodology and structures described in co-pending application serial no. PCT 01/24817, previously cited.

A tensile member 76 preferably extends adjacent the support body 66, shown parallel with fluid conduit 68, but not limited to such arrangement. The tensile member 76 may extend directly adjacent fluid conduit 68, or alternatively, be wrapped around the perimeter thereof. As may be appreciated, the tensile member 76 may be surplusage (i.e., redundant), being eliminated when fluid conduit 68 is sufficiently rigid or adequately reinforced. In the preferred architecture of this device, the tensile member is compressible along the longitudinal axis under a relatively light force, however, the tensile member may also be constructed of a material which is relatively stiff axially such as stainless steel wire.

The proximal anchor 58 generally includes body 64 and bladder engaging elements 60 radially extending therefrom. In contradistinction to heretofore known bladder discharge aides, urine may be released from the lowest part of bladder, often referred to as the bladder neck, urine being freely dischargable about/around an exterior surface of the body (i.e., a lateral flow condition) so as to substantially bathe the bladder neck.

The lateral urine flow path permitted by the proximal anchor, and the distal anchor as will later be presented, is beneficial for several reasons. First, the urine may more freely contact the bladder neck and bathe it. Second, the retained volume within the bladder is reduced following a urination event. Third, an internal passageway does not limit flow of urine to its boundaries. Urine may act in cooperation with the urethra. This is important. As an individual ages, the bladder function may weaken as a result of prostatic obstruction, or independently. The bladder micturition cycle is a work limited event. The muscle only contracts until it has spent the energy that is available to it. When the energy is spent, the muscles have tired, and will stop contraction regardless of the volume of urine remaining in bladder. This remaining urine is referred to as the post void residual (PVR), giving rise to at least two further implications. A high PVR requires a sooner return to the bathroom. If this is during sleeping hours, it will result in incomplete sleep and the deleterious effects associated therewith. Furthermore, a high PVR is widely viewed as contributing to at least the susceptibility to urinary tract infections.

The bladder engaging elements 60 of the proximal anchor 58 are advantageously circumferentially spaced apart about the surface of the anchor body 64. Preferably, but not necessarily, the engaging elements 60 are opposingly paired (FIG. 2A), but need not be so limited. It is further advantageous that the bladder engaging elements 60 be resilient, and preferably, be reversibly expandable (e.g., the bladder engagement elements 60 may be opposingly paired balloons as depicted in FIG. 2/2A). Preferably, the bladder engaging elements 60 are torpedo shaped when un-deflected by contact or otherwise unencumbered, this shape contributing only a minimum of flow resistance when properly filled. As is readily appreciated, low resistance is a critical consideration with respect to proper stable device placement within the lower urinary tract.

The interface of the resilient bladder engaging elements 60 relative to the anchor body 64 (or proximal segment 54 of elongate member 52), along with the methodology and structure (i.e., insertion/filling tool) for reversibly deploying such endourethral device, or devices of this style, is generally disclosed in applicant's co-pending PCT Application No. 01/24817, entitled ENDOURETHRAL DEVICE & METHOD, referenced herein above, any modification or adaptation thereto to accommodate the nature (i.e., structural) of the contemplated endourethral device being considered within the skill of person of ordinary skill in the art.

The proximal anchor 58 further includes at least a pair of urine flow channels 78, each of the channels being defined or otherwise delimited by adjacent bladder engaging elements 60, see especially FIG. 2A. The urine flow channels 78 provide for high volumetric flow rates, and relatively complete bathing of the urethra with urine (i.e., the notion of device flow about or around a/k/a lateral flow). Urine flow is initiated when the external sphincter is dilated by the natural function of the body at the users initiation. As will be later generally detailed with respect to FIGS. 8-9, the distal anchor 62 may, as in the device of FIG. 2, have elements, and interrelationships therebetween, which substantially corresponding to those of the proximal anchor 58.

With continued reference to FIG. 2A, which illustrates the endourethral device in situ as viewed axially from proximal extremity 80, proximal anchor 58 secures the urethral device 50 from moving into the urethra (not shown in this view). The elongate member 52 may be advantageously provided with a passageway or lumen 82 to allow for introductions of fluids such as drugs, or antiseptics, or for filling the bladder by an insertion/inflation tool. This optional passageway may be closed or open following device insertion, however, it is preferable that the device of FIG. 2 have a closed passageway following removal of insertion device, the closure limiting the area available for static urine to form encrustation.

Referring now generally to FIGS. 3-7 and FIGS. 3A-7A, there is presented alternate proximal anchor configurations (i.e., device structures or elements more broadly as the case may be) which permit, at a minimum, lateral flow, thereby contributing to the bathing effect, and to a minimal pressure profile for the device. Several proximal anchor configurations further provide for, or at least contemplate, the elongate member 52 including structure (e.g., a tubular segment) adapted to receive and permit the passage of urine therethrough, the tubular segment being positionable to reside within the prostatic urethra. This architecture for the device may be most beneficial for patients having particularly restrictive bladder outlets.

FIG. 3/3A illustrates the proximal portion or segment 54 of an endourethral device configured with a proximal anchor 158 having a body 164 and bladder engaging elements 160 radially extending therefrom. The anchor body 164 in this particular architecture is a portion of the proximal segment 54 of an elongate member, the body 164 having a twelve to sixteen French diameter, with an inner diameter of five to eight French. This configuration provides for the majority of the urine to pass around the perimeter of the proximal anchor. It is easily observed that the bladder engaging elements 160 of the proximal anchor 158 are shaped, as illustrated, into two pontoon-shaped projections. This resultant shape is achieved by bonding each of the bladder engaging elements 160 (e.g., balloons) along approximately 60 degrees on opposing sides of the proximal extent 54 of the elongate member (i.e., surface of the anchor body 164). The urine then may easily pass around the urine flow channels 178 on each side of the anchor body 164 into the bladder outlet. From there, the urine passes adjacent the axis of the device. Urine may also be received through an aperture 184 of the proximal end 54 of the elongate member, and thereby pass through the lumen 182 for discharge at the distally apertured opposing end 156 (i.e., distal portion not shown) of the elongate member, consistent with applicant's aforementioned co-pending subject matter.

FIG. 4/4A illustrate bladder engaging elements comprising spaced-apart, preferably padded, splines 260. The padded splines 260 radially extend from the exterior surface of, or are otherwise integral with, the surface of the anchor body 264, in this particular configuration, a proximal end portion 54 of the elongate member. The padded splines 260 include, or more particularly radially terminate in, a urinary tract engaging head 261 which provides an increased area for contact with the structures of same, thereby providing a more gentle engagement therewith. As the case with the configuration of FIGS. 3/3A, urine "flow through" may be advantageously achieved.

FIGS. 5/5A illustrate the proximal portion 54 of an elongate member, wherein the proximal portion 54 of a elongate member has a convex form 300, extending along or parallel to the longitudinal axis of the elongate member, on a portion of the circumference or outer surface thereof. This configuration, also contemplates opposingly paired splines 360 extending along the longitudinal axis of the elongate member 52. These splines 360, as the configuration of FIGS. 4/4A, provide for gentle support of the urethra while allowing delimited by the adjacent bladder engaging elements 360 relative to the surface of the proximal segment 54 of the elongate member, and further in this configuration, between the convex form 300 and each of the splines 360. One or more convex forms 300, or one or more splines 360 may be provided.

FIGS. 6/6A illustrate a further proximal anchor configuration wherein at least a portion of the proximal segment 54 of an elongate member is configured similarly to that of FIG. 4/4A, more particularly, exhibiting a cruciform cross-section, less the heads 261 of the splines 260 of that style, with the addition of a curl 402 integral to the proximal segment 54 of the elongate member. The radially extending urinary tract engaging portions 460 of the elongate member 52 (i.e., the terminal ends or extremities of each of the cruciform segments or splines) support the urethra in an open condition by contact of the splines 460 while allowing urine to flow between the urethra and the recesses 478 so delimited thereby (i.e., by adjacent splines of the cruciform).

Finally, with respect to the proximal anchor, FIGS. 7/7A illustrates a combination of previously described arrangements. Circumferentially spaced apart radially extending balloons 560 are carried at or near the proximal segment 54 of an elongate member having a general cruciform cross-section, that is to say, the proximal segment 54 is a profiled element, having a plurality of spaced apart radially extending ribs 563, more particularly, opposingly paired radially extending ribs 563 which allow urine to flow between the urethra and the recesses 578 so delimited thereby (i.e., by adjacent ribs of the cruciform).

Referring now to FIGS. 8/8A & 9, an endourethral device 650, similar in general arrangement to that shown in FIG. 2 (i.e., having a common proximal anchor feature and elongate member comprising a helical support element), is shown incorporating a distal flow around anchor mechanism 662. The distal anchor 662 preferably, but not necessarily, includes a body 665 and urethral engaging elements 661 extending therefrom. More particularly, the urethral engaging elements 661 are circumferentially disposed, in a spaced apart condition, about an exterior surface of the distal anchor body 665, the elements 661 being radially extendible therefrom. The distal anchor 662 further includes at least a pair of urine flow channels 678, each of the channels 678 being delimited by adjacent urethral engaging elements 661. It should be readily appreciated that anchoring of an endourethral device may be satisfactorily accomplished by a proximal segment 654, distal segment 656, or a sharing of anchor function between each.

Endourethral device 650 has a proximal extremity 654 and a distal extremity 656. FIG. 8 illustrates device 650 having proximal anchor member (e.g., balloon) 664 and distal anchor member (e.g., balloon) 662 in a "filled" condition (i.e., the anchor elements of the device are in extension) whereas FIG. 9 illustrates device 650 without fluid in proximal anchor member 664 or distal anchor member 662 (i.e., the anchor elements of the device are in retraction). FIG. 8A is a centerline cross section of distal anchor 662 of FIG. 8 illustrating filling conduit 668 in fluid communication with the interior of distal anchor 662. As may be appreciated, urine may easily flow adjacent distal anchor body 665 within the bulbous urethra. This particular device 650 may be best described in 4 sequentially aligned zones, namely, moving distally from the proximal end of the elongate member, zones I, II, III, and IV.

A passageway 682 extends through a first zone I from orifice 684 of the proximal end 654 of the elongate member 652. A second zone II, which dwells in the prostatic urethra consists of an open structure, namely an open pitched coil, which continues within a wall of the proximal portion 654 of the elongate member 652, and terminates by or in unified construction or attachment to a tensile member 676 (zone II zone III) which further terminates in the distal zone IV containing anchor 662. The tensile member 676 also converges or attaches to the extremity of proximal segment 654 for safety. The internal fluid communication between the first zone I and the distal anchor 662 is accomplished through conduit 668 which is shown axially separate from tensile member 676 though they are preferably in close proximity, or the same element.

The open structure of this endourethral device allows for the urine to contact the wall of the urethra and flow along the urethra as it drains. This has the beneficial effect, as likewise achieved via the structure of FIG. 2, of allowing for the natural secretions from the prostatic gland into the urethra to participate in their natural environment. These secretions are known to be beneficial as natural infection inhibitors as well as participating in sexual functions. Tensile member 676 is preferably constructed of a silicone coated silk suture material, or alternatively of a more rigid material such as a coated stainless steel wire.

Referring now generally to FIGS. 10-20, a mechanical distal anchor 762 is illustrated for an endourethral device, more particularly a wing type structure is shown tethered to an elongate member of an endourethral device. As emphasized throughout, a variety of devices may advantageously integrate the new anchor structures of the subject invention, singularly or in combination. For instance, the device of FIG. 10 illustrates heretofore known proximal anchoring in combination with mechanical anchor 762. In this style device, a circumferentially disposed bladder (shown uninflated in FIG. 11) is carried about the outer surface of a proximal portion of the elongate member for fully engaging a portion of the bladder neck. Proximally of the proximal anchor, the proximal portion of the elongate member is adapted, as via the inclusion of an aperture or plurality of same, to receive urine for passage interiorly of the elongate member (e.g., a tubular element). The device of FIG. 12 depicts an endourethral device having the flow around or lateral flow proximal anchor as shown and previously described with respect to FIG. 2.

As with all distal segments, those depicted are designed to be placed in the urethra in the bulbous urethra. The distal segments are interconnected with the proximal segment via a tether, preferably a silicone coated silk material which is soft and pliable, e.g., a surgical suture, or alternately, may comprise a more rigid element, even to the stiffness of a stainless steel wire of up to a 0.025" diameter. For example, with reference to the device of FIG. 10, securing threads 756 are tied and encapsulated near the distal extremity of body 765, and extend to the distal anchor. These threads may be provided either pre-tied to provide a fixed initial length, or adjustable to provide the physician the ability to adjust per his/her measurement requirements. Distal anchor 762 is mechanical in nature without inflatable components.

Referring again generally to FIGS. 10-14A, the distal anchor 762 (or 862 (FIG. 12/12A), 962 (FIG. 13/13A), 1062 (FIG. 14/14A), 1162 (FIG. 15), 1262 (FIG. 16), 1362 (FIG. 17), 1462 (FIG. 18), 1562 (FIGS. 19), and 1662 (FIG. 20)) generally includes a body 765 having urethral engaging elements or portions 761 extending or depending therefrom, or otherwise integral thereto. As is readily appreciated by a review of the figures, the distal anchor element 762 is of particularly low profile (i.e., an insubstantial hindrance to urine discharge), being reversibly expanded following deployment (e.g., by discharge from an insertion tool or the like). The mechanical anchor preferably tapers toward a distal end thereof, such configuration aiding the retrieval of the mechanical anchor as will be discussed.

The distal anchor 762 preferably, but not necessarily, includes a silicone encapsulated spring strut 786, or particular arrangement of struts or strut segments, either directly or indirectly extending from a central hub 788. When resiliently expanded, as for instance post deployment, the struts 786 expand to discretely engage portions of the urethral wall. In the configuration of FIG. 12A, it is noted that a portion of the elongate member 852 possesses a cruciform cross-section resulting from radially extending circumferentially spaced apart ribs 863.

As is best shown with respect to FIGS. 13-14A, the generally curved or arcuate, or at a minimal curvable, distal anchor may have a deployed "c" shaped, or other curved/arced cross section during, or upon deployment, within the bulbous urethra. It is the nature of the distal anchor to approach a static, maximally dimensioned (i.e., laterally dimensioned) condition post deployment. The resilient mechanical distal anchor may be longitudinally deformable (i.e., resiliently deformable throughout at least some portion of its length, as by having opposing lateral edges acted upon so as to approach each other (FIGS. 13A and 14A)).

Common to the depictions of FIGS. 12-14A, the mechanical anchor 862 is tethered or otherwise joined so as to distally extend from the distal portion 856 of the elongate member 852. A retrieval tether 890 is fixed to an extremity or end of the distal anchor 862 to facilitate removal of the device generally, and is further joined to drain tether 892 and removal tether 893. The mechanisms and functions of the tethers are fully detailed, along with associated methodologies, in the aforementioned co-pending applications incorporated herein by reference.

Referring now generally to FIGS. 15-22, there is presented alternate distal anchor configurations (i.e., device structures or elements more broadly as the case may be) which permit, at a minimum, lateral flow, thereby contributing to the bathing affect, and to a minimal pressure profile for the device. Not all of the following configurations are mechanical, some relying upon the introduction of fluid for the reversible expansion (i.e., the anchor element itself may not be inherently resilient as the previously discussed anchor wing). It is preferable that the distal anchor be mechanical in nature, a more direct, expedient and reliable deployment being achieved.

Figure 15:
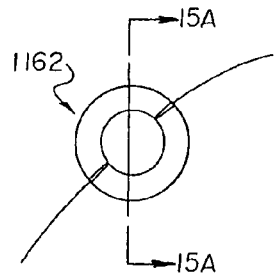
Figure 15A:
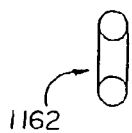

FIGS. 15/15A illustrate a single ring (i.e., "o-ring") distal anchor element. This mechanism is placed in tension during the insertion procedure, causing the o-ring to deform to an oval or oval-like profile which may be easily introduced into the urethra. When it is appropriately positioned, releasing of the applied tension allows the element to return to (i.e., approach) the relaxed state or condition. This anchor element may then substantially conform to the bulbous urethra. Removal of the device is accomplished by grasping a single tensile member so as to thereby effectively elongate the element for ease of removal.

Figure 16:
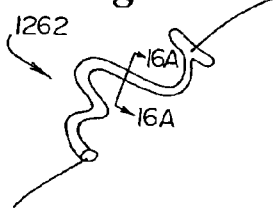
Figure 16A:
Figure 17:
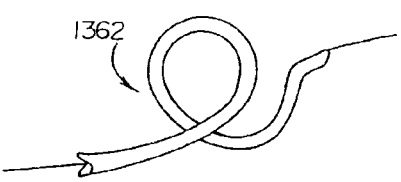
Figure 18A:
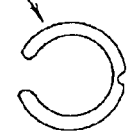
Figure 18:
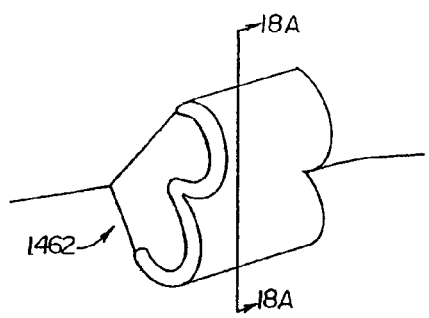
Figure 19:
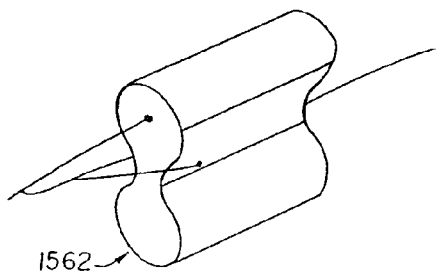
Figure 20:
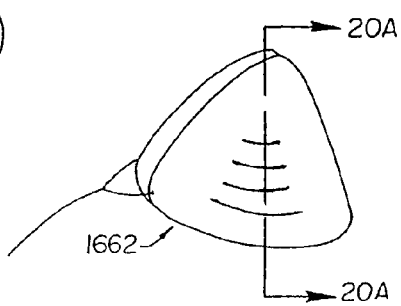
Figure 20A:

FIGS. 16/16A illustrate an anchor element comprising a partial non-uniform coil in a relaxed state, more particularly a profiled longitudinal element having compressible opposing lateral edges. This element, as the configuration of FIG. 15, is engaged and disengaged via manipulation of a tether threadingly traversing the element. Similarly, FIGS. 17-20, and the corresponding sectional views thereof, illustrate alternate resiliently expansible (i.e., reversible compressible) anchor elements readily manipulated by the aforementioned tether arrangements.

As to preferred materials of construction, relative to the device of FIG. 2 for example, the endourethral device generally utilizes a core construction of a 304 stainless steel wire coil encapsulated using implant grade silicone rubber (shore 30A, Rhoda Silicones, Inc., Ventura, Calif. PN V40029A & V40029B) to form a prostatic urethral stent. The proximal anchor of the device is bonded to the prostatic stent portion of the device. Bonding an anchoring balloon to a cast proximal tip forms the proximal anchor. The proximal tip is cast from silicone rubber (Rhoda Silicones). The anchoring balloon is extruded using an implant grade silicone rubber (NuSil Technology, Carpenteria, Calif., PN MED-4720), with the balloon being bonded using silicone adhesive (NuSil Tech. PN MED1-4213).

The distal anchor is formed in the same fashion as the proximal anchor; a balloon is bonded to a distal anchor manifold. The proximal anchor and distal anchor are connected via an inflation lumen which is a medical grade silicone rubber tube (SF Medical, Hudson, Mass.; PN SFM3-1350) possessing a 0.020" internal diameter and a 0.009" wall thickness. The tube is attached to each anchor using silicone adhesive.

The distal anchor manifold provides the location for receiving the drain plug of the anchoring balloons. The drain plug is formed from 304 stainless steel hypodermic tubing bonded/sealed to a size I/O silk suture using medical grade epoxy (TRA-CON, INC., Bedford, Mass.; PN TRA-BOND FDA2). When the plug is pulled from the distal anchor manifold port both the proximal and distal anchoring balloons deflate.

The device preferably uses a retrieval suture formed by size 1/0 silk suture, which is attached both to the distal end of the distal anchor and the distal end of the prostatic stent section. The retrieval suture traverses the length of the prostatic stent and attaches to the proximal end of the stent thereby limiting the amount of stent extension under tension. The use of silk provides flexibility due to its multiple strand construction while maintaining an acceptable break load limit.

The endourethral device may been fabricated in various lengths ranging from 4 to 9 cm (length measured from the distal end of the proximal balloon to the proximal end of the distal balloon). The ratio of the length of the prostatic stent to the remaining length (length spanning the external sphincter) may be varied, presently the length ratio is 3:2 (i.e. for a 5 cm length device, the prostatic stent length is 3 cm). The external profile of the device may be fabricated from 10 French to 32 French.

The devices of each of these embodiments may be coated with materials such as hydrogels or anti-microbial, or antibiotics. Alternatively these materials may be compounded into the silicone or polyurethane materials in order to achieve the desired inhibition of various bacteria. Silver oxide, or silver alloys are known for their inhibitive effect in the urinary tract. As may be appreciated, the structural elements such as stainless steel provide visualization by various methods such as abdominal or rectal ultrasound. They further provide visualization via cystoscopy, or x-ray. It may be further appreciate that beneficial materials may be applied to the surfaces of compounds of the device to alter the characteristics for purposes of visualization, pharmaceutical effect, anti-microbial effect, or friction. It is further expressed that variation of materials does not deviate from the spirit of the inventions of this patent. These additions are anticipated for certain patient populations.

This invention disclosure provides device configurations which achieve a sought after anchoring function and methodology. There are other variations of this invention which will become obvious to those skilled in the art. It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claim. As will further be appreciated, it is contemplated that the anchoring configurations of the subject invention be readily incorporated into known endourethral devices for diagnosis, managing or treating urological disorders, the benefits thereby accruing thusly being available generally to patient's presenting with such disorders.

What is claimed is:

1. An endourethral device comprising sequentially arranged proximal, prostatic, sphincter and distal segments, said proximal segment including a bladder anchoring element, said distal segment including a urethral anchoring element, said prostatic segment including an elongate member for maintaining a patency of a prostatic urethra, said elongate member includes a pharmaceutical agent and comprises a distal portion, said sphincter segment comprising an anchor tether which extends from said distal portion of said elongate member so as to unite said urethral anchoring element to said elongate member, said urethral anchoring element comprising a tapered resilient body including deformable urethral engaging portions.

2. The endourethral device of claim 1 wherein said elongate member includes a coating of said pharmaceutical agent.

3. The endourethral device of claim 1 wherein a portion of said elongate member includes a coating of said pharmaceutical agent.

4. The endourethral device of claim 1 wherein said elongate member comprises a material compounded so as to include said pharmaceutical agent.

5. The endourethral device of claim 1 wherein said pharmaceutical agent comprises a bacteria inhibiting agent.

6. The endourethral device of claim 5 wherein said bacteria inhibiting agent comprises a coating.

7. The endourethral device of claim 5 wherein said elongate member comprises a material compounded so as to include said bacteria inhibiting agent.

8. The endourethral device of claim 5 wherein said bacteria inhibiting agent comprises an anti-microbial agent.

9. The endourethral device of claim 8 wherein said anti-microbial agent comprises a coating.

10. The endourethral device of claim 8 wherein said elongate member comprises a material compounded so as to include said anti-microbial agent.

11. The endourethral device of claim 1 wherein said tapered resilient body includes a hub and strut segments extending therefrom, said deformable urethral engaging portions including portions of said strut segments.

12. The endourethral device of claim 11 wherein said elongate member includes a coating of said pharmaceutical agent.

13. The endourethral, device of claim 1 wherein a portion of said elongate member includes a coating of said pharmaceutical agent.

14. The endourethral device of claim 1 wherein said elongate member comprises a material compounded so as to include said pharmaceutical agent.

15. The endourethral device of claim 11 wherein said pharmaceutical agent comprises a bacteria inhibiting agent.

16. The endourethral device of claim 15 wherein said bacteria inhibiting agent comprises a coating.

17. The endourethral device of claim 15 wherein said elongate member comprises a material compounded so as to include said bacteria inhibiting agent.

18. The endourethral device of claim 15 wherein said bacteria inhibiting agent comprises an anti-microbial agent.

19. The endourethral device of claim 18 wherein said anti-microbial agent comprises a coating.

20. The endourethral device of claim 18 wherein said elongate member comprises a material compounded so as to include said anti-microbial agent.

21. The endourethral device of claim 1 further comprising a retrieval tether, said anchor tether extends through said urethral anchoring element so as to unite with a portion of said retrieval tether.

22. The endourethral device of claim 21 wherein said elongate member includes a coating of said pharmaceutical agent.

23. The endourethral device of claim 21 wherein a portion of said elongate member includes a coating of said pharmaceutical agent.

24. The endourethral device of claim 21 wherein said elongate member comprises a material compounded so as to include said pharmaceutical agent.

25. The endourethral device of claim 21 wherein said pharmaceutical agent comprises a bacteria inhibiting agent.

26. The endourethral device of claim 25 wherein said bacteria inhibiting agent comprises a coating.

27. The endourethral device of claim 25 wherein said elongate member comprises a material compounded so as to include said bacteria inhibiting agent.

28. The endourethral device of claim 25 wherein said bacteria inhibiting agent comprises an anti-microbial agent.

29. The endourethral device of claim 28 wherein said anti-microbial agent comprises a coating.

30. The endourethral device of claim 28 wherein said elongate member comprises a material compounded so as to include said anti-microbial agent.

31. An endourethral device comprising sequentially arranged proximal, prostatic, sphincter and distal segments, said proximal segment including a bladder anchoring element, said distal segment including a urethral anchoring element, said prostatic segment including an elongate member for maintaining a patency of a prostatic urethra, said elongate member includes a pharmaceutical agent and comprises a distal portion, said sphincter segment comprising an anchor tether which extends from said distal portion of said elongate member so as to unite said urethral anchoring element to said elongate member, said urethral anchoring element comprising a resilient body including deformable urethral engaging portions.

* * * * *